(12) United States Patent
Demos

(10) Patent No.: US 8,285,015 B2
(45) Date of Patent: Oct. 9, 2012

(54) SIMULTANEOUS ACQUISITION OF DIFFERING IMAGE TYPES

(75) Inventor: Stavros G. Demos, Livermore, CA (US)

(73) Assignee: Lawrence Livermore Natioonal Security, LLC, Livermore, CA (US)

(*) Notice: Subject to any disclaimer, the term of this patent is extended or adjusted under 35 U.S.C. 154(b) by 1109 days.

(21) Appl. No.: 12/167,104

(22) Filed: Jul. 2, 2008

(65) Prior Publication Data

US 2008/0267472 A1    Oct. 30, 2008

Related U.S. Application Data

(63) Continuation-in-part of application No. 11/796,689, filed on Apr. 27, 2007, which is a continuation of application No. 10/400,024, filed on Mar. 25, 2003, now Pat. No. 7,257,437, which is a continuation-in-part of application No. 10/190,231, filed on Jul. 5, 2002, now Pat. No. 7,016,717.

(60) Provisional application No. 60/958,557, filed on Jul. 6, 2007.

(51) Int. Cl.
*G06K 9/00* (2006.01)
*A61B 6/00* (2006.01)

(52) U.S. Cl. .................. 382/128; 600/473; 600/476

(58) Field of Classification Search .......... 600/407–476; 382/128, 133; 359/368; 356/301, 317
See application file for complete search history.

(56) References Cited

U.S. PATENT DOCUMENTS

| | | | |
|---|---|---|---|
| 3,817,633 A | 6/1974 | White | 356/97 |
| 4,930,516 A | 6/1990 | Alfano et al. | 128/665 |
| 4,957,114 A | 9/1990 | Zeng et al. | 128/665 |
| 5,042,494 A | 8/1991 | Alfano et al. | 128/665 |
| 5,131,398 A | 7/1992 | Alfano et al. | 128/665 |

(Continued)

FOREIGN PATENT DOCUMENTS

EP   0352952 A2 *   7/1988

(Continued)

OTHER PUBLICATIONS

Timothy R. Corle and Gordon S. Kino; "Chapter 2—Instruments"; Confocal Scanning Optical Microscopy and Related Imasging Systems; 1996; pp. 67-145.*

(Continued)

*Primary Examiner* — Ella Colbert
(74) *Attorney, Agent, or Firm* — Dominic M. Kotab

(57) ABSTRACT

A system in one embodiment includes an image forming device for forming an image from an area of interest containing different image components; an illumination device for illuminating the area of interest with light containing multiple components; at least one light source coupled to the illumination device, the at least one light source providing light to the illumination device containing different components, each component having distinct spectral characteristics and relative intensity; an image analyzer coupled to the image forming device, the image analyzer decomposing the image formed by the image forming device into multiple component parts based on type of imaging; and multiple image capture devices, each image capture device receiving one of the component parts of the image. A method in one embodiment includes receiving an image from an image forming device; decomposing the image formed by the image forming device into multiple component parts based on type of imaging; receiving the component parts of the image; and outputting image information based on the component parts of the image. Additional systems and methods are presented.

14 Claims, 4 Drawing Sheets

U.S. PATENT DOCUMENTS

| | | | | |
|---|---|---|---|---|
| 5,261,410 | A | | 11/1993 | Alfano et al. .................. 128/664 |
| 5,313,306 | A | * | 5/1994 | Kuban et al. ..................... 348/65 |
| 5,348,018 | A | | 9/1994 | Alfano et al. .................. 128/665 |
| 5,467,767 | A | | 11/1995 | Alfano et al. .................. 128/665 |
| 5,593,879 | A | | 1/1997 | Steller et al. ............... 435/240.1 |
| 5,769,081 | A | | 6/1998 | Alfano et al. .................. 128/665 |
| 5,833,596 | A | * | 11/1998 | Bonnell et al. ................. 600/109 |
| 5,847,394 | A | | 12/1998 | Alfano et al. ............... 250/341.8 |
| 5,976,076 | A | * | 11/1999 | Kolff et al. ..................... 600/166 |
| 5,997,472 | A | * | 12/1999 | Bonnell et al. ................. 600/109 |
| 6,169,289 | B1 | | 1/2001 | White et al. ................ 250/458.1 |
| 6,269,169 | B1 | | 7/2001 | Funk et al. ..................... 382/100 |
| 6,413,267 | B1 | | 7/2002 | Dumoulin-White et al. ... 607/89 |
| 6,462,770 | B1 | * | 10/2002 | Cline et al. ....................... 348/65 |
| 6,477,403 | B1 | * | 11/2002 | Eguchi et al. .................. 600/478 |
| 6,529,769 | B2 | * | 3/2003 | Zigler ............................. 600/478 |
| 6,598,428 | B1 | | 7/2003 | Cryan et al. ...................... 65/409 |
| 6,687,000 | B1 | | 2/2004 | White ............................. 356/328 |
| 6,730,019 | B2 | * | 5/2004 | Irion ............................... 600/178 |
| 6,775,567 | B2 | * | 8/2004 | Cable et al. .................... 600/407 |
| 6,949,069 | B2 | * | 9/2005 | Farkas et al. ................... 600/178 |
| 6,975,898 | B2 | | 12/2005 | Seibel ............................. 600/473 |
| 6,975,899 | B2 | | 12/2005 | Faupel et al. ................... 600/476 |
| 7,003,147 | B2 | * | 2/2006 | Inoue ............................. 382/132 |
| 7,016,717 | B2 | | 3/2006 | Demos et al. .................. 600/473 |
| 7,172,553 | B2 | * | 2/2007 | Ueno et al. ..................... 600/160 |
| 7,257,437 | B2 | | 8/2007 | Demos et al. .................. 600/473 |
| 2001/0030744 | A1 | * | 10/2001 | Chang ......................... 356/237.3 |
| 2003/0158470 | A1 | * | 8/2003 | Wolters et al. ................. 600/317 |
| 2003/0232445 | A1 | * | 12/2003 | Fulghum, Jr. .................... 436/63 |
| 2005/0020926 | A1 | * | 1/2005 | Wiklof et al. ................. 600/476 |

FOREIGN PATENT DOCUMENTS

| | | | |
|---|---|---|---|
| EP | | 129364 A | 1/2003 |
| WO | WO/02/38040 A | | 5/2002 |

OTHER PUBLICATIONS

U.S. Appl. No. 11/292,406, filed Nov. 30, 2005.

Udagawa, M., et al., "Aberrant Porphyrin Metabolism in Hepatocellular Carcinoma," Biochemical Medicine 31, pp. 131-139, Cedemic Press, Inc. (1984).

Pitts, J., et al.. "Autofluoresrence characteristics of Immortalized and carcinogen-transformed human bronchial epithelial cells," Journal of Biomedical Optics 6(1), pp. 31-40 (Jan. 2001).

Zawirska, B., "Comparative Porphyrin Content in Tumors with Contiguous Non-Neoplastic Tissues," Neoplasma 26 , 2, pp. 223-229 (1979).

Malik, Z., ct al., "Destruction of crythoroleukaemic cells by photoactivation of endogenous porphyrins," Health sciences Research Center, Dept. of Life Sciences, Bar-Ilan University, Ramat-Gan 52100, Israel, 7 pages, (Mar. 9, 1987).

Zhang, G, et al., "Far-red and NIR Spectral Wing Emission from Tissue under 532 and 632 nm Photo-excitation,"Lasers in the Life Sciences, vol. 9, pp. 1-16 (1999).

Alfano, R., et al., "Laser Induced Fluorescence Spectroscopy from Native Cancerous and Normal Tissue,"IEEE Journal of Quantum Electronics, vol. QE-20, No. 12, pp. 1507-1511 (Dec. 1984).

Navone, N., et al., "Porphyrin biosynthesis in human breast cancer. Preliminary mimetic in vitro studies," Med. Sci. Res., 16, pp. 61-62., (1988).

Richards-Kortum, R., et al., "Spectroscopic Diagnosis of Colonic Dyspiasia," Photochemistry and Photobiology, vol. 53, No. 6, pp. 777-786, (1991).

Demos, S., et al., "Subsurface Imaging Using the Spectral Polarization Difference Technique and NIR Illumination," Lawrence Livermore National Laboratory, UCRL-JC-I31091 Preprint, 7 pages (Jan. 23, 1999).

Demos, S., et al., "Tissue Imaging for cancer detection using NIR autofluorescence, "Lawrence Livermore National Laboratory, 8 pages (May 2002).

Schomacker, K., et al. , "Ultraviolet Laser-Induced Fluorescence of Colonic Tissue: Basic Biology and Diagnostoc Potential," Lasers in Surgery and Medicine, 12, pp. 63-78, (1992).

\* cited by examiner

SIMULTANEOUS ACQUISITION OF DIFFERING IMAGE TYPES

RELATED APPLICATIONS

This application claims priority to provisional U.S. application Ser. No. 60/958,557 filed on Jul. 6, 2007, which is herein incorporated by reference. This application is also a continuation-in-part of U.S. application Ser. No. 11/796,689 filed on Apr. 27, 2007, which is a continuation of U.S. application Ser. No. 10/400,024 filed on Mar. 25, 2003 now U.S. Pat. No. 7,257,437 which is a continuation-in-part of U.S. application Ser. No. 10/190,231 filed Jul. 5, 2002 now U.S. Pat. No. 7,016,717, priority of each of which is hereby claimed, and each of which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to image acquisition, and more particularly to simultaneous formation, transfer, decomposition and/or capture of multi-spectral and or multi-modal images.

BACKGROUND

While visual examination still remains the most important diagnostic method, recent rapid progress in photonic technologies for real time pathological assessment has demonstrated a great deal of promise by expanding the dimension and spectral range of observation. The spatial resolution of these new technologies extends from the tissue to the single cell level and can provide information in real time to help enhance the ability of a surgeon to determine the status of tissue. Development of technology capable of providing diagnostic information in real time could revolutionize a number of diagnostic and therapeutic clinical procedures.

Optical biopsy utilizes optical spectroscopy techniques to characterize tissue, and requires direct exposure of the tissue under examination to the light source. It is therefore particularly suitable in a clinical setting for intraoperative use to assist in the assessment of the tissue in real time. Numerous reports over the past 20 years have highlighted a number of spectroscopic approaches capable of detecting cancer and separating out the different tissue components. An example of such a technology is described in U.S. application Ser. No. 10/400,024 filed on Mar. 25, 2003, from which priority is claimed.

Tissue characterization via photonic techniques explores the use of intrinsic optical signatures (contrast mechanisms) or extrinsic contrast agents to detect and/or image abnormal (such as cancer) tissues and organs in real time. Although basic research has provided the proof of concept that a number of different approaches can provide histopathology information in real time, to date there has been limited success in translating this photonic technology into novel medical instrumentation. Arguably, this may be yet another example of a new technology that industry fails to recognize its potential in a timely fashion or a failure by scientists to design and build instrumentation suitable for use in a clinical setting that has the potential to emerge from the basic research level.

SUMMARY

A system in one embodiment includes an image forming device for forming an image from an area of interest containing different image components; an illumination device for illuminating the area of interest with light containing multiple components; at least one light source coupled to the illumination device, the at least one light source providing light to the illumination device containing different components, each component having distinct spectral characteristics and relative intensity; an image analyzer coupled to the image forming device, the image analyzer decomposing the image formed by the image forming device into multiple component parts based on type of imaging; and multiple image capture devices, each image capture device receiving one of the component parts of the image.

A system in one embodiment includes an image analyzer for coupling to an image forming device adapted for insertion in a human body, the image analyzer decomposing an image formed by the image forming device into multiple component parts based on type of imaging; multiple image capture devices, each image capture device receiving one of the component parts of the image; and a processing device coupled to the image capture devices.

A method in one embodiment includes receiving an image from an image forming device; decomposing the image formed by the image forming device into multiple component parts based on type of imaging; receiving the component parts of the image; and outputting image information based on the component parts of the image.

Other aspects and embodiments of the present invention will become apparent from the following detailed description, which, when taken in conjunction with the drawings, illustrate by way of example the principles of the invention.

DETAILED DESCRIPTION

Figure 1:
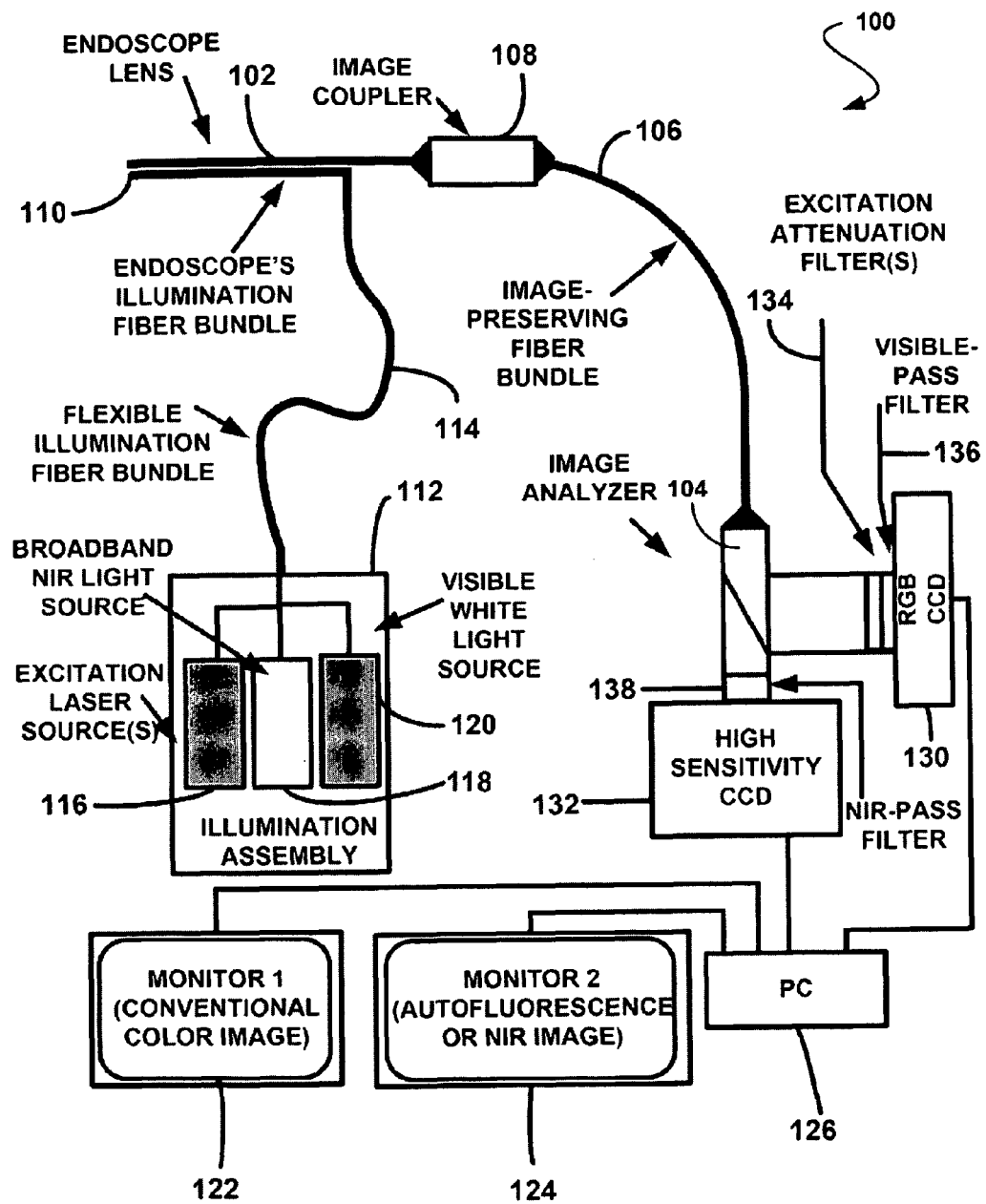
FIG. 1 illustrates a system for simultaneous acquisition of images using different techniques according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include-plural referents unless otherwise specified.

A system in one general embodiment includes an image forming device for forming an image from an area of interest containing different image components; an illumination device for illuminating the area of interest with light containing multiple components; at least one light source coupled to the illumination device, the at least one light source providing light to the illumination device containing different components, each component having distinct spectral characteristics and relative intensity; an image analyzer coupled to the image forming device, the image analyzer decomposing the image formed by the image forming device into multiple component parts based on type of imaging; and multiple image capture devices, each image capture device receiving one of the component parts of the image.

A system in one general embodiment includes an image analyzer for coupling to an image forming device adapted for insertion in a human body, the image analyzer decomposing an image formed by the image forming device into multiple component parts based on type of imaging; multiple image capture devices, each image capture device receiving one of the component parts of the image; and a processing device coupled to the image capture devices.

A method in one general embodiment includes receiving an image from an image forming device; decomposing the image formed by the image forming device into multiple component parts based on type of imaging; receiving the component parts of the image; and outputting image information based on the component parts of the image.

Instrumentation is described according to various embodiments that can be adapted to any type of image forming device (e.g., camera lenses, microscope lens, etc) of image forming and relaying devices (e.g. endoscopes, laparoscopes, boroscopes, endoscope-type devices used in the medical field to view interior body structures, etc.) that offers the ability to simultaneously acquire multiple optical images that are based on different methodologies. This may include simultaneous acquisition of two or more of the following (or other) types of images: conventional color (RGB) image, auto fluorescence images, image based on fluorescence of a contrast agent, polarization sensitive image, light scattering images at different spectral ranges, Raman scattering spectrum from a localized area, etc. In some approaches, the images can be acquired through a wide range of spatial resolutions. Moreover, imaging can be performed from the micro scale (e.g., cell level) to the macro scale (e.g., tissue level), and anywhere in between. Some embodiments also allow transitioning from one scale to another.

According to various embodiments, the instrumentation may be particularly suitable for medical applications when adapted to various types of endoscopic devices such as, e.g., colonoscopes, cystoscopes, laparoscopes, bronchoscopes, etc., to examine interior body organs and tissues using multiple optical spectroscopy-based imaging techniques while the conventional color image is simultaneously recorded so that several or all of the images can be displayed in real time. The benefit of such application is that the visual examination, which still remains the most important diagnostic method during surgery, is complemented by the spectral image(s) which can provide additional diagnostic information in the most efficient manner that allows for easy co-registration and correlation of image features and minimized acquisition time.

In one particularly preferred approach, novel instrumentation for tissue diagnosis provides expedited information and high sensitivity and specificity. One important parameter to be taken into account is the limited time a patient can spend in the operating room. This weighs heavily in favor of instrumentation that offers fast scanning speed. Consequently, in one approach, the main screening technique may be of low spatial resolution but at the same time, may provide high sensitivity. In other embodiments, an important issue is to be able to accurately assess the margins of a tumor. Margin delineation may require higher spatial resolution and also higher specificity. Several multimodal approaches presented herein incorporate high sensitivity and specificity. Moreover, the new technologies presented herein may be complementary to existing methodologies.

In various embodiments, the task of achieving integration of imaging methodologies (conventional and novel spectroscopic) includes acquiring all images simultaneously by the same image forming device (lens, endoscope, etc). Accordingly, one embodiment of the present invention includes instrumentation that can integrate acquisition in real time of color conventional imaging with spectral imaging or point spectroscopic measurements over a wide range of spatial resolutions. This instrumentation can preferably be adapted to any existing image forming device such as those already in use in the medical field. Furthermore, the design of such instrumentation may take into consideration the surgeon's work ergonomy. It is generally desirable that the tools used by the surgeon are lightweight and have physical dimensions compatible with the human anatomy.

While much of the following discussion focuses on the detection of cancer, this is done by way of example only. It should therefore be kept in mind that the same type of technology can be used to image and/or separate out various components in other types of tissue such as nerves, veins, arteries, tumors, scar tissue, foreign objects such as shrapnel, etc. Furthermore, it can be used to evaluate tissue components exposed to various adverse conditions such as ischemic or chemical injury and genetic defects. Other uses and applications are also anticipated.

One clinical setting particularly pertinent to the teachings herein is the detection and imaging of cancer located inside the body via endoscopes. Based on the discussion above, the design of an endoscopic system for real time cancer detection and margin delineation preferably affords fast screening speed, and the ability to examine the margins with high spatial resolution and high sensitivity and specificity. To achieve fast screening speed, one embodiment employs macroscopic dual imaging where a conventional color (red/green/blue, or RGB) or black and white image is displayed simultaneously with the spectral image to help determine abnormal tissue regions.

Any type of conventional color or black and white imaging technology can be used. Illustrative components are presented below.

The spectral image may be based on other types of imaging, such as auto fluorescence images, image based on fluorescence of a contrast agent, polarization sensitive image, light scattering images at different spectral ranges, Raman scattering spectrum from a localized area, etc. For example, optical biopsy utilizes optical spectroscopy techniques to characterize tissue, and requires direct exposure of the tissue under examination to the light source. It is therefore particularly suitable in a clinical setting for intraoperative use to assist in the assessment of the tissue in real time.

The spectral image may also be based on a wide range of photonic techniques. Tissue characterization via photonic techniques explores the use of intrinsic optical signatures (contrast mechanisms) or extrinsic contrast agents to detect and/or image abnormal (such as cancer) tissues and organs in real time.

The spectral image may be based on the utilization of the Near Infrared (NIR) Autofluorescence under long-wavelength excitation imaging technique in combination with NIR light scattering as described in U.S. Pat. No. 7,257,437 to Stavros et al., which is herein incorporated by reference.

FIG. 1 is a schematic diagram of an imaging system 100 according to one embodiment. As shown in FIG. 1, the system 100 includes an image forming device 102. The image forming device 102 used to form, and optionally relay, an image from the area of interest (e.g., tissue or internal organ) can be or include any conventional device such as camera lenses, various types of endoscopes designed to achieve direct visualization of objects located in a remote location, or other modality. Therefore, one embodiment of the system design presented here can be adapted to any existing image forming instrumentation already available at a user location.

An image transfer line 106, such as an image preserving fiber or fiber bundle, a conduit or channel having reflective portions, e.g., mirrors, etc., relays the image from the image forming device 102 to a separate location where the image can be retrieved, decomposed into individual components or modified via optical mechanisms. The resulting image information based on the capture device output, including raw or processed image data, can thereafter be directly displayed on the same or on separate output devices 122, 124 such as video monitors or other types of display devices, and/or further processed using appropriate computer software e.g., on a processing device 126, e.g., computer, chip, Application Specific Integrated Circuit (ASIC), etc., for output of information derived therefrom. Accordingly, as implied, each output device may display information corresponding to one or more of the component parts of the image. Moreover, images can be "fused" into composite images via software and/or hardware and output on one or more of the monitors 122, 124. In one approach, an NIR image is superimposed on a color image. The overlying image may be translucent, semitransparent, and/or nontranslucent. Further, the overlying image may include only portions of the source image, such as portions having a contrast or intensity in some range, or above or below a threshold value.

An illumination device 110 may be coupled to the image forming device 102. In one approach, an illumination channel of the endoscope 102 or other image forming device may be used to carry the illumination light from an illumination assembly 112 to the remote location to be imaged. The illumination device 110 may be integral to the image forming device 102, or coupled thereto. The illumination device 110 can also be free from the image forming device 102. In one approach, the illumination device 110 includes a fiber or fiber bundle that is part of the image forming device 102. Light from an illumination assembly 112 is carried to the illumination device 110 by appropriate transfer mechanism 114, such as a fiber or fiber bundle. The transfer mechanism 114 is preferably flexible. The illumination assembly 112 may include one or more light sources 116, 118, 120, as needed to illuminate the sample (organ, tissue, etc.) being imaged in the appropriate format. The light source(s) provide light to the illumination device containing different components, each component having distinct spectral characteristics and relative intensity. Illustrative light sources include broadband or narrow band NIR light sources, excitation laser sources, visible light sources, monochromatic light sources, other narrow band light sources, ultraviolet light sources, etc. For example, NIR spectral imaging may be based on light scattering from tissue, tissue autofluorescence, emission by a fluorescent contrast agent, etc.

In the illustrative embodiment of FIG. 1, the illumination includes a white light source 120 covering the visible spectrum to facilitate the acquisition of the conventional color image. In addition, laser sources 116, 118 are used to excite the tissue or a contrast agent (e.g., that has been applied to the tissue area to be imaged through topical application, the vascular system or other method) at the desired wavelength to produce the fluorescence signal to be used to form the spectral image.

In various approaches, the illumination light sources 116, 118, 120 may be coupled to the illumination channel that may already exist in the image relaying device 102. In the case of endoscopes, an illumination fiber is used to deliver light into the interior body location to be imaged. This same illumination channel can be used to deliver the output of the system's light sources into the location to be imaged.

Note that the image forming device 102 may be coupled directly to the image transfer line 106. Alternatively, the image formed by image forming device 102 may be coupled to the image transfer line 106 via the use of an image coupler 106 which is comprised mainly of a set of lenses to relay the image from the image forming device 102 to the image transfer line 106.

In other approaches, an optional image transfer module 108 may interface with the image forming device 102 to assist in coupling the formed image to the image transfer line 106. The image transfer line 106 is preferably flexible, or preferably has a flexible section to allow articulation of the image forming device 102. One vendor of fiber optic bundles that may be used in various embodiments is Schott Fiber Optics, Inc., d.b.a. SCHOTT North America, Inc., 555 Taxter Road, Elmsford, N.Y. 10523, USA. Types of fibers and fiber bundles that are usable with some embodiments are presented in U.S. Pat. No. 6,598,428 to Cryan et al., which is herein incorporated by reference for its teaching of fibers and fiber bundles.

In use, the image is retrieved at the distal end of the image transport line 106 using appropriate optics 108 and projected towards an image analyzer 104 that splits the image into component parts, which are directed towards two or more different image recording devices 130, 132, e.g., cameras, after being split. The image analyzer 104 may include devices that reflect light at certain wavelengths and allow light at other wavelengths to pass therethrough. Decomposition or "splitting" of the conventional color image may be achieved using a "cold" minor which allows for the image component in the visible range to be reflected towards a first image capture device (e.g., RGB CCD) 130. The remaining (NIR) component of the image passes through the "cold" mirror and is recorded by a second image capture device 132 (e.g., high sensitivity CCD array). Moreover, any of the information may be recorded and stored, e.g., electronically on a hard disk or tape library, in raw form, processed form, compressed or converted form, etc.

Appropriate filters may be used in front of each imaging/detection system to exclude some or all of the spectral components not needed for the execution of the specific task by each component. For example, an excitation attenuation filler 134 may be used to filter out laser light from the image applied to a color image capture device 130. A visible light pass filter 136 may also be used in conjunction with a color image capture device 130. For a NIR image, for example, an appropriate NIR-pass filter 138 may be used.

This technique allows for the separation of the conventional RGB image from the NIR spectral image (or any other combination of images) so that both can be acquired and displayed simultaneously. In addition, as mentioned previously, the spectral image in some approaches can be based on fluorescence or light scattering. In the latter case, the Spectral and Polarization Differential Imaging technique (SPDI) can be used to achieve depth profiling of a suspected lesion or tissue components (such as veins or arteries) providing additional diagnostic capabilities. The SPDI image can be acquired through an additional imaging module that employs simultaneous acquisition of light scattering images at different wavelengths. SPDI imaging may require additional illumination wavelengths/sources and filters as has been described in U.S. Pat. No. 7,257,437 to Stavros et al., which has been incorporated by reference.

For tumor margin delineation (or other applications where higher spatial resolution images are needed), regions of interest (suspected cancer) may be examined at the microscopic level to visualize tissue microstructure (organization and cell characteristics) using autofluorescence imaging under UV excitation. These approaches have been described in U.S. patent application Ser. No. 11/292,406 "Hyperspectral microscope for in vivo imaging of microstructures and cells in tissues", filed on Nov. 30, 2005, and which is herein incorporated by reference. This approach can be integrated into the system design described here. Implementation of such approach may include endoscopes that have zoom capabilities or utilization of more than one endoscope, each providing the desired spatial resolution.

To achieve a high level of specificity, imaging/screening using multiple optical modalities/techniques may be employed. To address this problem, one embodiment has built-in multimodal and multispectral imaging capabilities for both, the macro- and micro-scopic imaging modes. For example, for the macroscopic imaging module, imaging at different parts of the NIR spectrum can be utilized while the excitation (used for autofluorescence or contrast agent fluorescence imaging) may be at any (or multiple) wavelengths shorter than about 670-nm. Multimodal imaging can also be used in the microscopic imaging module. For example, excitation around 270-nm provides images based on tryptophan emission while excitation around 330-nm provides images based on collagen or NADH which can be separated out by selecting the appropriate spectral window for imaging (centered at 390-nm for collagen and 470-nm for NADH). These images can be acquired simultaneously (e.g 266-nm excitation and 300-330-nm emission for tryptophan along with 355-nm excitation and 370410 nm emission for collagen and 430-520-nm emission for NADH). In addition, the spectral range for excitation may be expanded in the visible to acquire images based on emission by other tissue fluorophores (such as Flavins and Porphyrins) or contrast agents. A schematic layout of a system according to one embodiment that incorporates RGB color imaging, NIR fluorescence imaging, SPDI imaging and three different modes of microscopic imaging (e.g., as described above) is shown in FIG. 2.

Figure 2:
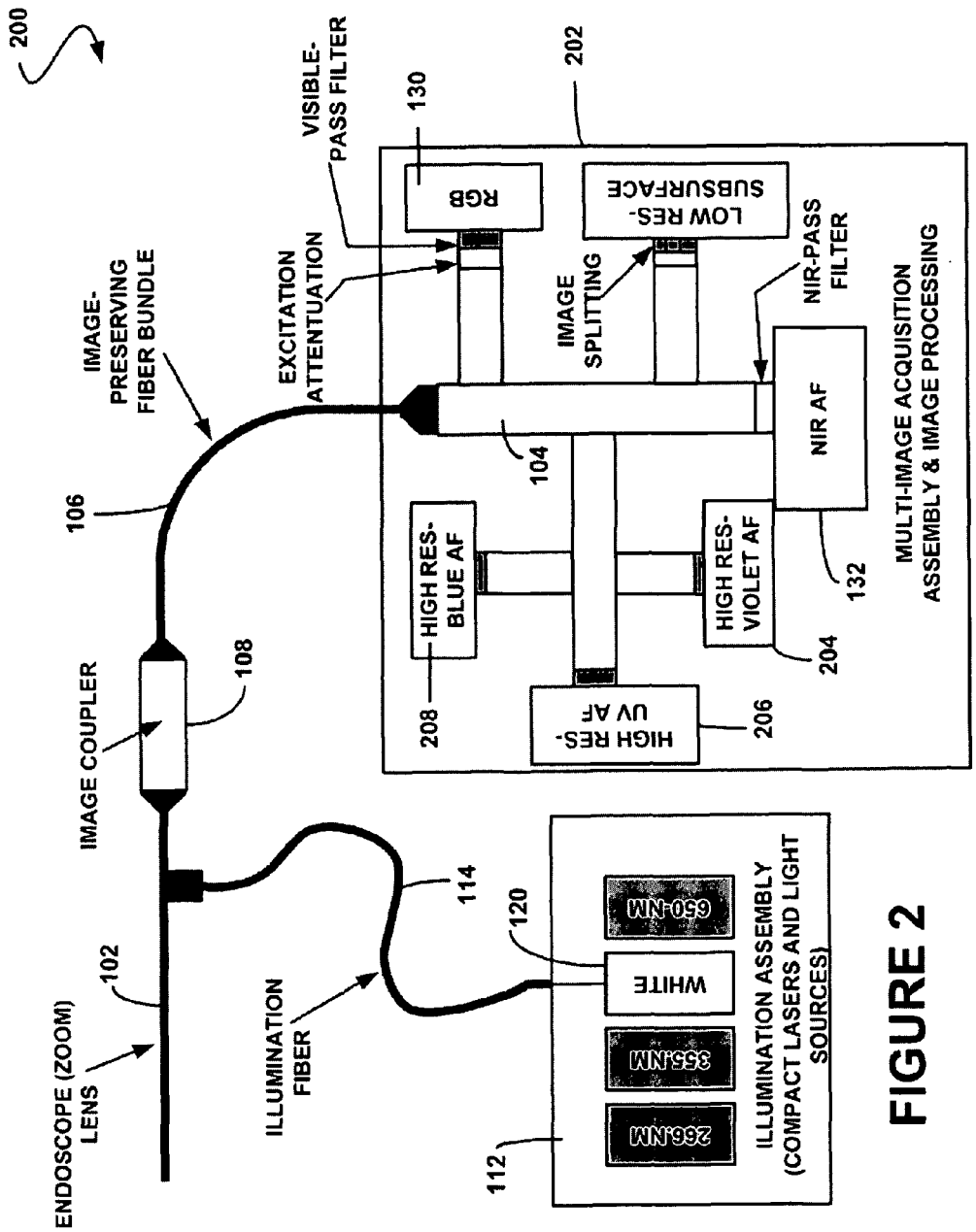
FIG. 2 illustrates a system for simultaneous acquisition of images using different techniques according to one embodiment.

Referring to the illustrative embodiment 200 of FIG. 2, similar general components as in the system 100 of FIG. 1 are used. Again, a commercially available endoscope (possibly with zoom capabilities) or other type of image forming device 102 can be used for multi-image acquisition. The endoscope is used to form and relay the images of interior body organs (esophagus, bladder, colon, etc.) and/or tissues into an image preserving fiber bundle 106. The image is then transferred into the image processing unit 202 where it is split to individual components (imaging modes) such as conventional color (RGB), SPDI (low resolution subsurface), fluorescence (low resolution autofluorescence or contrast agent) and three microscopic images in the blue, violet and ultraviolet spectrum. All images can be acquired simultaneously via image capture devices 130, 132, 204, 206, 208 and displayed separately and/or fused into composite images via software or hardware, etc.

As in the systems of FIG. 1, appropriate filters may be used in front of each imaging/detection system to exclude some or all of the spectral components not needed for the execution of the specific task by each component.

Figure 3:
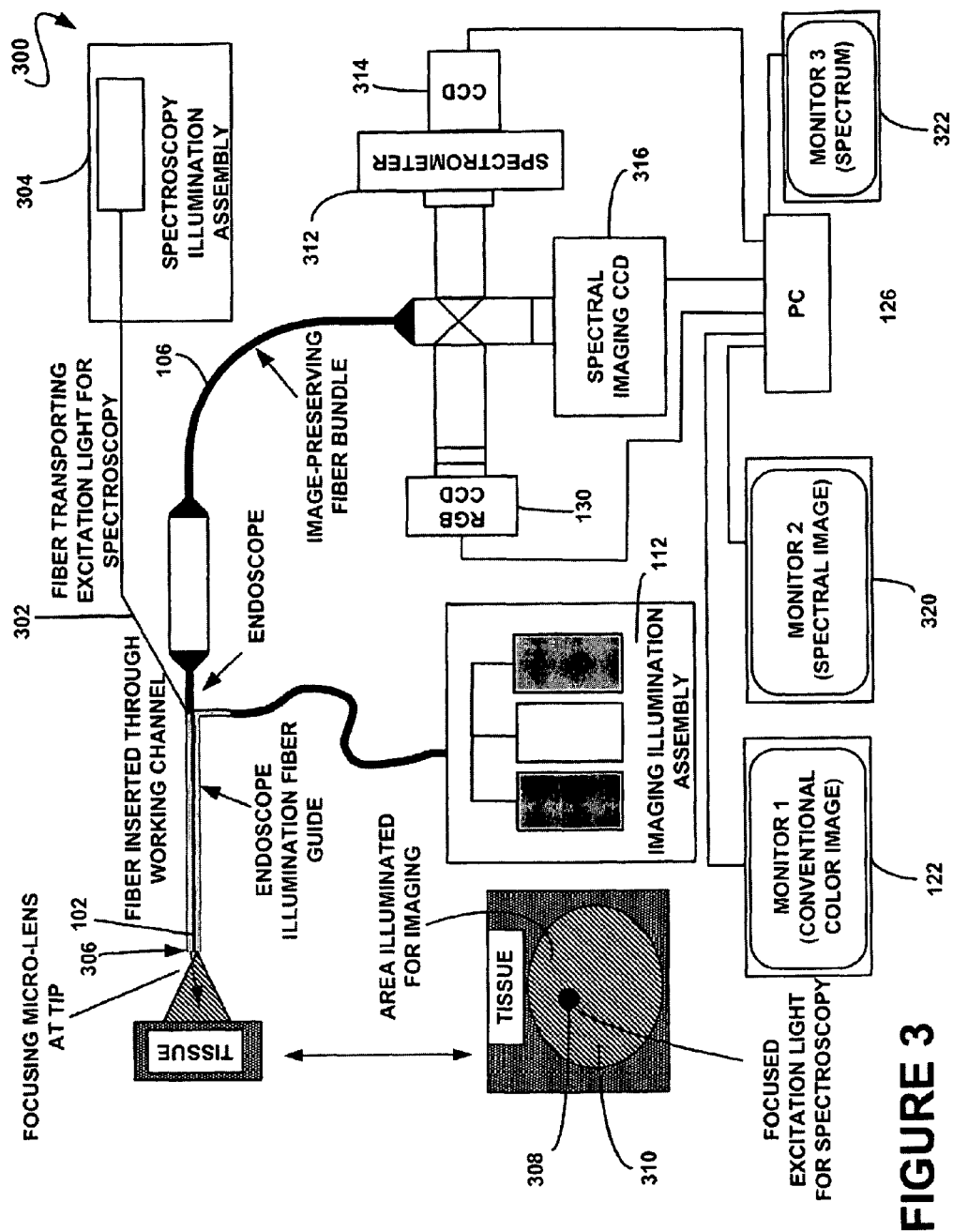
FIG. 3 illustrates a system for simultaneous acquisition of images using different techniques according to one embodiment.

The imaging approaches described above can be complemented by the acquisition of the spectrum from a single smaller region within the imaged area. One illustrative system 300 having this type of instrumentation is shown in FIG. 3, which shows a design for the simultaneous acquisition of a spectral image (such as NIR autofluorescence or contrast agent emission) along with a color RGB image that are complemented by acquisition of the spectral profile (such as Raman scattering) from a smaller area. The execution of this type of measurement that involves simultaneous acquisition of images and spectral profiles from a single point involves a number of modification/addition to the designs previously described. First, the excitation light (laser) to be used for spectroscopy is preferably delivered by a separate illumination channel 302 such as a fiber that is passed from a second illumination assembly 304 and through the working channel of the image forming device 102, e.g., endoscope, to reach the target area. A microlens 306 (such as a grin lens) located at the tip of the fiber is used to focus the light into a small area (point-like) 308 within the imaged area 310 (which may be illuminated using the endoscope's illumination channel or through a separate illumination guide external or internal to the endoscope). The spectrum (e.g., fluorescence, Raman scattering, etc.) is collected by the image forming system (lens or endoscope) and preferably projected into a specific set of fibers in the image transfer line 106, e.g., image preserving fiber bundle, that correspond to the area 308 of the image that is illuminated by the focused excitation source. At the distal end of the image preserving fiber 106, the image may be split again similarly to the way it was described above, but part of the image containing the spectral region where the spectral profile is located is directed into the slit of a spectrograph 312. The part of the image that does not contain the spectral information (not illuminated by the focused light source) may be discarded via the use of a device (such as a pinhole) that allows for spatial selection of the signal from a specific area of the image prior to entering the slit (or equivalent apparatus such a pinhole or input fiber) of the spectrometer 312. The spectrum may be spectrally resolved and recorded by an appropriate device 314 (such as a CCD). Another spectral imaging device 316 may acquire a different spectral image (such as NIR autofluorescence or contrast agent emission) while a color image capture device 130 captures a color RGB image. As above, representations of the various images can be displayed on monitors 122, 320, 322; processed by a computing device 126; superimposed on one another; etc. Note that the information output relating to the spectral profile from the smaller area may be representative data showing some computed result based on the spectral image received.

As a example of possible implementation of the system shown in FIG. 3, the specific spectral ranges used by each modality may be the following: 1) The RGB image is obtained using white light illumination in the 400-650 nm spectral range. 2) The NIR autofluorescence or contrast agent emission image is obtained Linder 650 nm excitation and emission in the 680-790 nm spectral range. 3) To record the Raman scattering spectrum from a specific location within the imaged area, laser excitation at 800-nm is utilized while the Raman scattering spectrum of the tissue extends from 810-950 nm.

As in the systems of FIGS. 1 and 2, appropriate filters may be used in front of each imaging/detection system to exclude all other spectral components except the one needed for the execution of the specific task by each component.

Figure 4:
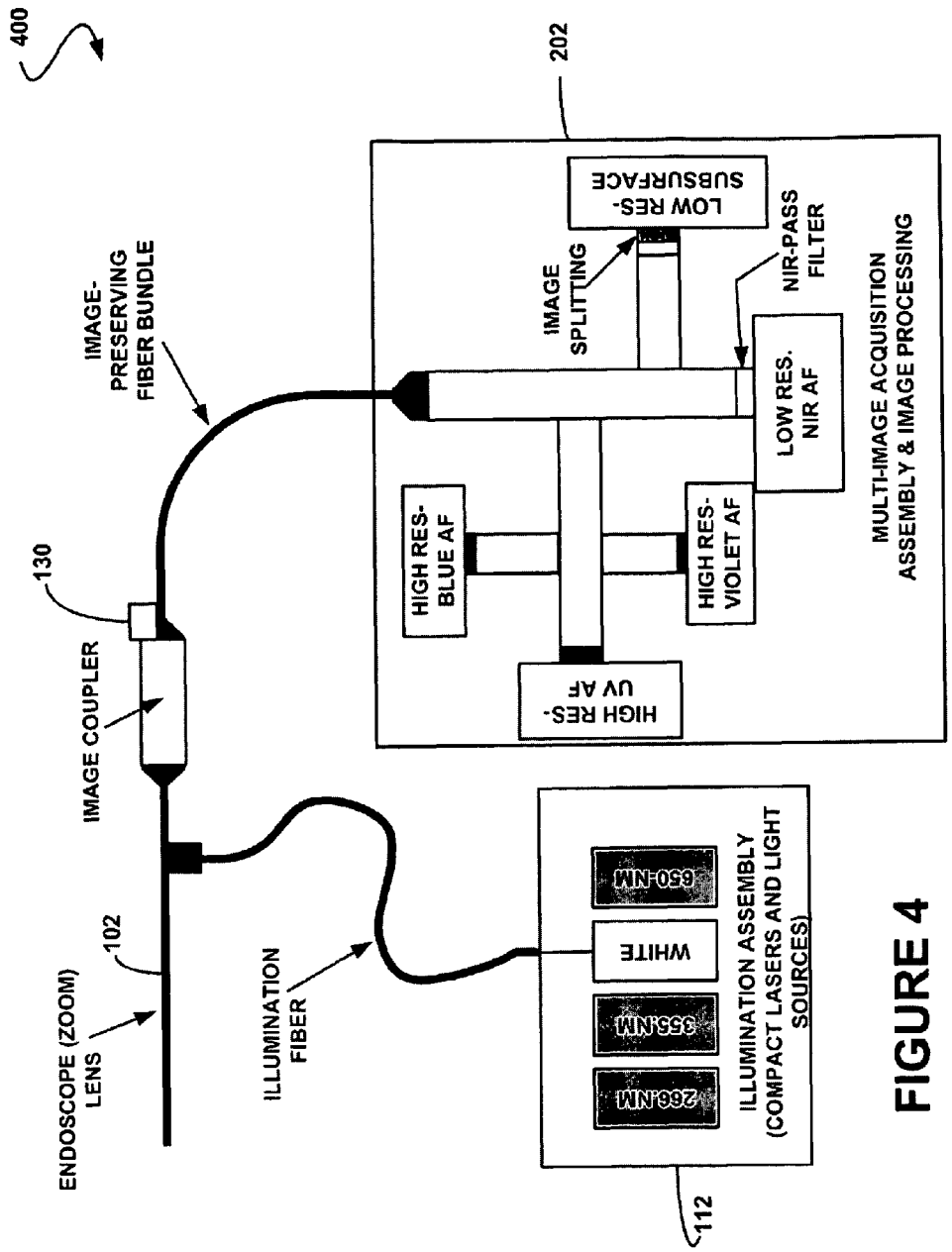
FIG. 4 illustrates a system for simultaneous acquisition of images using different techniques according to one embodiment.

FIG. 4 depicts yet another illustrative embodiment 400 in which an image is captured nearer to the image forming device 102. Accordingly, an image capture device may be coupled to the image forming device 102, the image transfer module 108, a first splitter, etc. In the approach shown, a RGB CCD 130 is coupled to the image transfer module 108. The color image is split from the remaining image at the image transfer module 108, and the remaining image passes through the image transport line 106 to another image capture device and/or image processing unit 202. Typically, the resolution of the recorded image formed by the image forming device 102 is dependent upon the number of fibers in a fiber bundle of the image transfer line 106. This approach, for instance, more readily allows capture of a higher resolution color image and lower resolution NIR image through a fiber bundle.

The embodiments described herein, and the many variations and permutations thereof, have many novel aspects. For instance, some embodiments include integration of different imaging modalities into a single system that can be used for in vivo screening and interrogation of tissue in a clinical setting aiming at providing sufficient information to achieve in real time a) histopathology evaluation, b) surface or subsurface tissue component visualization and separation, and c) tissue evaluation. In some embodiments, the spectral image(s) are simultaneously acquired and displayed with a conventional color (RGB) image which helps minimize the extra time for implementation of the new imaging method(s) (e.g., no need to insert a specialized endoscope) while the operator can directly correlate the spectra image or spectral profile with the images he/she is trained to utilize as the primary guidance tool.

Uses of the Embodiments

Embodiments of the present invention may be used in a wide variety of applications, and potentially any application in which imaging is useful.

Illustrative uses of various embodiments of the present invention include, but are not limited to detection and diagnosis of disease, cancer detection and imaging, detection and imaging of other tissue pathologies, detection and analysis of cellular processes, microscopy, multi-spectral and hyper-spectral imaging, separation and imaging of tissue components, endoscopy and interior body imaging, remote sensing and imaging, etc.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
an image analyzer for coupling to an image forming device adapted for insertion in a human body, the image analyzer decomposing an image formed by the image forming device into multiple component parts based on type of imaging;
multiple image capture devices, each image capture device receiving one of the component parts of the image; and
a processing device coupled to the image capture devices, wherein the processing device is configured to acquire and process image data from the multiple image capture devices in real tune and provide a new composite image based on the component parts.

2. The system of claim 1, further comprising at least one light source for providing light to an illumination device coupled to the image forming device for delivering illumination into the area of interest.

3. The system of claim 2, further comprising the image forming device and an illumination channel, the illumination channel being configured such that light from the illumination channel is focused onto a smaller portion of the area of interest than that illuminated by the illumination device.

4. The system of claim 3, further comprising a spectrometer equipped with a capture device for receiving light from the image analyzer originating from the smaller portion of the area of interest that is illuminated by the focused light of the illumination channel.

5. The system of claim 2, wherein the at least one light source includes a first light source for generating ultraviolet, far red, near infrared or infrared light and a second light source for generating visible white light.

6. The system of claim 2, wherein the at least one light source includes a broadband visible light source and at least one other light source for inducing tissue autofluorescence outside of a visible spectrum or fluorescence from the tissue outside of a visible spectrum in the presence of a fluorescence contrast agent.

7. The system of claim 2, wherein the at least one light source includes a visible light source and at least one other light source for generating broadband or multiple narrow bands in the far red and near infrared (NIR) spectral region.

8. The system of claim 1, wherein the image forming device includes a single endoscopic or endoscopic microscope or a device that can provide endoscopic imaging from the microscopic to the macroscopic level.

9. The system of claim 1, wherein composite image information based on multiple component parts of the image is output.

10. The system of claim 1 wherein the image forming device is a handheld or robotically held device that can view an interior or exterior of a human body.

11. The system of claim 10, wherein the image forming device provides spatial resolution capable of viewing tissue organization and structure at a cellular level.

12. The system of claim 10, wherein the image forming device provides a user-selectable spatial resolution.

13. A system, comprising:
an image analyzer for coupling to an image forming device adapted for insertion in a human body, the image analyzer decomposing an image formed by the image forming device into multiple component parts based on type of imaging;
multiple image capture devices, each image capture device receiving one of the component parts of the image; and
a processing device coupled to the image capture devices; and
output devices coupled to the processing device,
wherein the processing device is configured to acquire and process image data from the multiple image capture devices simultaneously, the output devices being for displaying information based on the image data acquired from the image capture devices.

14. A system, comprising:
an image analyzer for coupling to an image forming device adapted for insertion in a human body, the image analyzer decomposing an image formed by the image forming device into multiple component parts based on type of imaging;
multiple image capture devices, each image capture device receiving one of the component parts of the image;

a processing device coupled to the image capture devices;
the image forming device; and
an illumination channel, the illumination channel being configured such that light from the illumination channel is focused onto a smaller portion of the area of interest than that illuminated by the illumination device,
wherein the image capture devices are configured to operate independently, continuously, and simultaneously to capture image data, and wherein the processing device is configured to process image data captured from the multiple image capture devices in real time and output one or more composite images that are based on the component parts including an image based on one of the component parts superimposed over an image of another of the component parts.

\* \* \* \* \*